United States Patent
Reisinger et al.

(10) Patent No.: US 9,920,309 B2
(45) Date of Patent: Mar. 20, 2018

(54) ENZYME-COMPOSITION FOR HYDROLYZING BIOMASS

(71) Applicant: Clariant International Ltd., Muttenz (CH)

(72) Inventors: Christoph Reisinger, Munich (DE); Lutz Roecher, Munich (DE); Michael Kraus, Munich (DE); Christian Gamauf, Munich (DE)

(73) Assignee: CLARIANT INTERNATIONAL LTD., Muttenz (CH)

( * ) Notice: Subject to any disclaimer, the term of this patent is extended or adjusted under 35 U.S.C. 154(b) by 0 days.

(21) Appl. No.: 15/101,974

(22) PCT Filed: Dec. 15, 2014

(86) PCT No.: PCT/EP2014/077833
§ 371 (c)(1),
(2) Date: Jun. 6, 2016

(87) PCT Pub. No.: WO2015/097017
PCT Pub. Date: Jul. 2, 2015

(65) Prior Publication Data
US 2016/0304848 A1 Oct. 20, 2016

(30) Foreign Application Priority Data
Dec. 23, 2013 (EP) .................. 13006045.2

(51) Int. Cl.
| | |
|---|---|
| *C12P 19/14* | (2006.01) |
| *C12N 9/42* | (2006.01) |
| *C12N 9/24* | (2006.01) |
| *C12P 19/02* | (2006.01) |

(52) U.S. Cl.
CPC ......... *C12N 9/2437* (2013.01); *C12N 9/2402* (2013.01); *C12N 9/2477* (2013.01); *C12P 19/02* (2013.01); *C12P 19/14* (2013.01); *C12Y 302/01004* (2013.01); *C12Y 302/01015* (2013.01); *C12Y 302/01099* (2013.01)

(58) Field of Classification Search
None
See application file for complete search history.

(56) References Cited

U.S. PATENT DOCUMENTS

| | | | |
|---|---|---|---|
| 4,338,399 A | 7/1982 | Weil et al. | |
| 4,886,672 A | 12/1989 | De Baynast De Septfontaines et al. | |
| 6,132,727 A * | 10/2000 | Rohde, Jr. ...... | C12Y 302/01004 424/725 |
| 9,005,936 B2 * | 4/2015 | Koltermann ............ | C12P 19/02 435/99 |

FOREIGN PATENT DOCUMENTS

| | | |
|---|---|---|
| WO | 199529598 A1 | 11/1995 |
| WO | 2010136404 A2 | 12/2010 |
| WO | 2011045387 A1 | 4/2011 |

OTHER PUBLICATIONS

Olsson et al. (Enzyme & Microbi. Tech., vol. 33, p. 612-619).*
Rattanachomsri, U., et al., "Simultaneous non-thermal saccarification of cassava pulp by multi-enzyme activity and ethanol fermentation by Candida tropicalis," Journal of Bioscience and Bioengineering, Elsevier, May 1, 2009, , vol. 107, No. 5, pp. 488-493.
Hernández-Salas, J.M., et al., "Comparative hydrolysis and fermentation of sugarcane and agave bagasse," Bioresource Technology, Elsevier BV, Feb. 1, 2009, vol. 100, No. 3, pp. 1238-1245.
Spagnuolo, M., et al., "Synergistic effects of cellulolytic and pectinolytic enzymes in degrading sugar beet pulp," Bioresource Technology, Elsevier BV, Jun. 1, 1997, vol. 60, No. 3, pp. 215-222.
Pandey, A., et al., "Simultaneous Saccharification and Protein Enrichment Fermentation of Sugar Beet Pulp," Biotechnology Letters, 1988, vol. 10, No. 1, pp. 67-72.
Loginov, M., et al., "Comparison of dead-end ultrafiltration behaviour and filtrate quality of sugar beet juices obtained by conventional and "cold" PEF-assisted diffusion," Journal of Membrane Science, Elsevier, 2011, vol. 377, pp. 273-283.
Hinkova, A., et al., "Potentials of separation membranes in the sugar industry," Separation and Purification Technology, Elsevier, 2002, vol. 26, pp. 101-110.
Hatziantoniou, D., et al., "Influence of the properties and characteristics of sugar-beet pulp extract on its fouling and rejection behaviour during membrane filtration," Desalination, Elsevier, 2002, vol. 148, pp. 67-72.
Hakimzadeh, V., et al., "The potential of microfiltration and ultrafiltration process in purification of raw sugar beet juice," Desalination, Elsevier, 2006, vol. 200, pp. 520-522.
Beldman, G., et al., "Application of cellulase and pectinase from fungal origin for the liquefaction and saccharification of biomass," Butterworth & Co, Acrigultural University, Enzyme Microb. Technol., Nov. 1984, vol. 6, pp. 503-507.
Schaffeld, G., et al., "Sequential Acid and Enzymic Hydrolysis of Sugar Beet Pulp," J. Chem. Tech. Biotechnology 1987, vol. 39, pp. 161-171.
Shahidi, M., et al., "Improving thin sugar beet juice quality through ultrafiltration," Desalination, Elsevier, 2006, vol. 200, pp. 518-519.
International Search Report and Written Opinion, dated Mar. 24, 2015, issued in PCT/EP2014/077833.
Endo-1,5-alpha-Arabinanase Aspergillus niger for research; Megazyme—Setting New Standards in Test Technology.

* cited by examiner

*Primary Examiner* — Hope Robinson
(74) *Attorney, Agent, or Firm* — Gianna Julian-Arnold; Saul Ewing Arnstein & Lehr LLP

(57) ABSTRACT

The present invention is directed to an enzyme-composition for hydrolyzing biomass containing comprising at least one cellulase, at least one hemicellulases and/or at least one pectinases. In a further aspect, the present invention is directed to a process for hydrolyzing biomass implementing this enzyme-composition and the use of the enzyme-composition for hydrolyzing biomass.

5 Claims, 4 Drawing Sheets

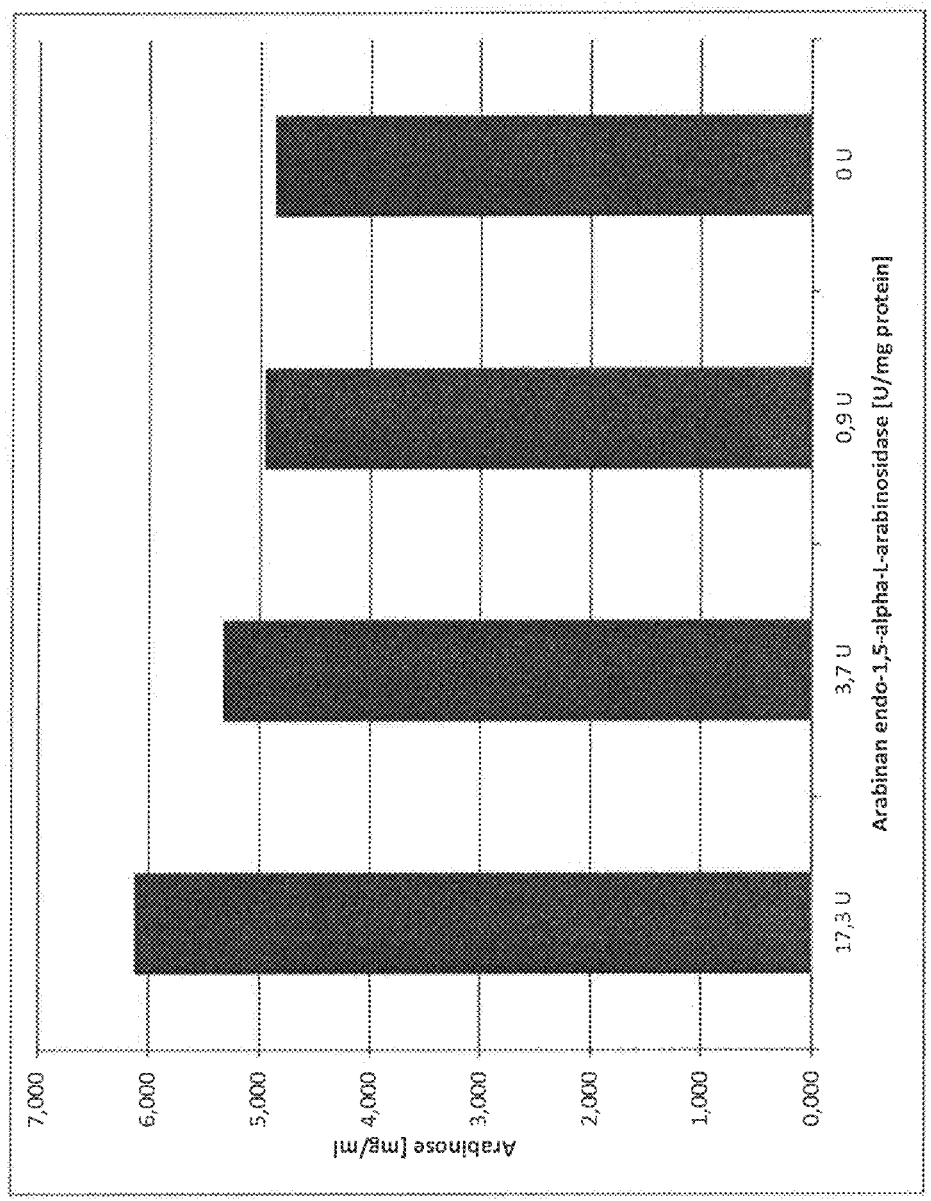

ENZYME-COMPOSITION FOR HYDROLYZING BIOMASS

CROSS REFERENCE TO RELATED APPLICATIONS

This application claims the priority of PCT/EP2014/077833, filed on 15 Dec. 2014, which claims priority to European Patent Application No. 13006045.2, filed 23 Dec. 2013, the entire contents of each of which are hereby incorporated in total by reference.

The present invention is directed to an enzyme-composition for hydrolyzing biomass comprising at least one cellulase, at least one hemicellulase and at least one pectinase. In a further aspect, the present invention is directed to a process for hydrolyzing biomass implementing this enzyme-composition and the use of the enzyme-composition for hydrolyzing biomass.

Biomass originating from sources such as sugar beet, corn, straw and other saccharide- or polysaccharide- and pectin-containing material is a valuable source for refined saccharides such as monomeric or dimeric sugars.

Within the state of the art, various processes have been applied to separate or extract these compounds from said biomass. Usually, these processes enable the simple separation or extraction of monomeric and dimeric sugars from the biomass material such as sugar-beet, however, the majority of saccharide-containing compounds such as cellulose, hemicellulose, lignin and/or pectin are regularly discarded.

Within a well established process monomeric and dimeric sugar is removed from e.g. sugar beets by extracting shredded sugar beets with hot water in a continuous counter-flow process. Usually, these processes require the addition of further agents such as CaO in an amount of around 1 to 3 kg of CaO per 100 kg of sugar beet. Products of this process are the sugar solution called raw juice and the so-called beet pulp, the latter being dried in a pulp dryer. The raw juice moves through various stages of purification and filtration to remove impurities and non-sugar substances to yield thick juice (65 to 70% dry matter content) or, after crystallization, refined fine sugar. The elevated temperature and pH conditions during this process cause the destruction of a crucial amount of monomeric sugars contained in the solution due to formation of acidic and coloured compounds. Further, due to the decomposition of nitrogen compounds with particular reference to amides ammonia is released in the atmosphere. In addition, the so called beet-pulp still contains not only the majority of proteins of the sugar beets but also the majority of polysaccharides such as cellulose, hemicellulose and pectin. According to the German Zuckerverband, in 2011/2012, a total of 4.266.670 t sugar was produced in Germany (given as "t Weißzuckerwert") corresponding to 1.907.302 t Schnitzel ("remnant") (indicated as "t Trockenschnitzelwert"). As a consequence, roughly 0.45 t remnant per t sugar arise as waste material (www.zuckerverbaende.de/zuckermarkt/zahlen-und-fakten/zuckermarkt-deutschland/ruebenanbau-zuckererzeugung.html).

To overcome these drawbacks, other possibilities of degradation of biomasses have been tested such as the use of hydrolytic enzymes. There are already commercial enzyme-compositions originating from natural fungal sources available for the hydrolysis of biomass e.g. the product "Pectinex®" containing pectinases, hemicellulases and cellulases as an side activity and the product "Celluclast®" containing mainly cellulases and hemicellulases (both by Novozymes®). The use of such commercial products is described within the U.S. Pat. No. 4,886,672 and the EP 2 256 208 A1.

Until now, these products are, however, barely applicable to major-scale production processes as the degradation-rate of biomass is still relatively low. Thus, the process time necessary for a substantial hydrolysis of the biomass is still considerably high and therefore the application of these commercially available products for industrial purposes is limited.

Thus, there is a need for a novel and high-performing enzyme-composition which enables the complete degradation and/or hydrolysis of saccharide and/or polysaccharide containing biomass within reasonable time. Further, there is a need within the state of the art for such a high-performing enzyme-composition which can be cost-efficiently produced in high quantities. In addition, there is a need for such a high-performing enzyme-composition which can be applied to industrial-scale hydrolyzation-processes.

It is thus the object underlying the present invention to provide a process for hydrolyzing biomass which does not show any of the disadvantages of the processes known within the state of the art.

It has now been surprisingly found by the inventors of the present invention that the problems associated with enzyme-compositions known within the state of the art can be solved by an enzyme-composition comprising at least one cellulase, at least one hemicellulase and at least one pectinase, wherein the at least one hemicellulase comprises an Arabinan endo-1,5-alpha-L-arabinosidase (EC 3.2.1.99) with an arabinan degrading activity of at least 10 U/mg protein.

The terms "cellulase", "hemicellulase" and "pectinase" as used within the present invention refer to any enzyme which is involved in the hydrolytic scission of polymeric cellulose, hemicellulose and/or pectin, respectively, to monomeric sugars. As used herein, the terms "cellulase", "hemicellulase" and "pectinase" refer to both naturally occurring and non-naturally occurring enzymes or blends that include a plurality of enzymes as produced by an organism, for example a filamentous fungus. "Cellulases", "hemicellulases" and "pectinases" are preferably derived from fungi such as members of the subdivision Eumycota and Oomycota, including but are not limited to the following genera: Aspergillus, Acremonium, Aureobasidium, Beauveria, Cephalosporium, Ceriporiopsis, Chaetomium, Chrysosporium, Claviceps, Cochiobolus, Cryptococcus, Cyathus, Endothia, Endothiamucor, Fusarium, Gilocladium, Humicola, Magnaporthe, Myceliophthora, Myrothecium, Mucor, Neurospora, Phanerochaete, Podospora, Paecilomyces, Pyricularia, Rhizomucor, Rhizopus, Schizophylum, Stagonospora, Talaromyces, Trichoderma, Thermomyces, Thermoascus, Thielavia, Tolypocladium, Trichophyton, and Trametes. In a preferred implementation, the filamentous fungus is a Trichoderma species.

Within a preferred embodiment of the enzyme-composition according to the present invention the at least one cellulase, hemicellulase and/or pectinase is from a fungal source. Within a particularly preferred embodiment of the enzyme-composition according to the present invention, this fungal source is Trichoderma reesei.

The term "blend of enzymes" preferably refers to a blend of enzymes secreted from one or more microbial sources. In some embodiments, enzymes for use in these blend(s) of enzymes can be prepared from one or more naturally occurring or engineered strains of filamentous fungi. Preferred strains are listed above. The desired ratio of enzyme components within the final blend(s) can be achieved by altering the relative amount of enzyme in the final blend e.g. by supplementation of purified or partially purified enzyme(s).

As used within the present invention, the term "cellulase" refers to any enzyme or blend of enzymes capable of hydrolyzing cellulose polymers to shorter oligomers and/or glucose.

The at least one cellulase within the enzyme composition according to the present invention is preferably selected from cellobiohydrolases (EC 3.2.1.-), endo-1,4-β-glucanase (EC 3.2.1.4), β-glucosidase (EC 3.2.1.4), cellobiose hydrolase (EC 3.2.1.21), glycoside hydrolase 61 (GH61 and CBM33), Expansin, Swollenin, Loosinin and CIP Proteins (EC 3.1.1.-; CE15).

Within a preferred enzyme-composition the term "cellulase" comprises at least one enzyme selected from the group of cellobiohydrolases (EC 3.2.1.-) and endo-1,4-β-glucanase (EC 3.2.1.4).

As used within the present invention, the term "hemicellulase" refers to any enzyme or blend of enzymes capable of degrading or supporting the degradation of hemicellulose.

The term "Arabinan endo-1,5-alpha-L-arabinosidase" refers to Arabinan endo-1,5-alpha-L-arabinosidase EC 3.2.1.99. Within the present invention the Arabinan endo-1,5-alpha-L-arabinosidase EC 3.2.1.99 has an arabinan degrading activity of at least 10 U/mg protein, preferably at least 15 U/mg protein, further preferred at least 20 U/mg protein, particularly preferred at least 40 U/mg protein and most preferred at least 50 U/mg protein. Further preferred the arabinan degrading activity is selected from the range from 10 to 100 U/mg protein, preferably 10 to 65 U/mg protein, further preferred from 20 to 65 U/mg protein and from 20 to 50 U/mg protein.

Arabinan endo-1,5-alpha-L-arabinosidase as used within the enzyme composition of the present invention may be expressed by a bacterial or fungal source. Arabinan endo-1,5-alpha-L-arabinosidase is preferably derived from fungi such as *Aspergillus terreus, Bacillus subtilis, Aspergillus oryzae, Fomes fomentarius, Penicillium chrysogenum, Aspergillus aculeatus, Cylindro carponcongoense, Nectria haematococca, Myceliophthora thermophile, Chaetomium globulosum, Trametes versicolor* or *Aspergillus nidulans*. The Arabinan endo-1,5-alpha-L-arabinosidase may be produced by expression in an endogenous organism or may be produced by expression in a heterologous organism. Preferably, the primary and accessory enzymes are produced by expression in *Trichoderma reesei*.

In case there is one or more further hemicellulase(s) contained within the enzyme composition according to the present invention besides Arabinan endo-1,5-alpha-L-arabinosidase, this one or more hemicellulase is preferably selected from β-glucanases (EC 3.2.1.-), endo-xylanase (EC 3.2.1.8), β-xylosidase (EC 3.2.1.37), acetylxylan esterase (EC 3.1.1.72), acetylgalactan esterase (3.1.1.6), acetyl mannan esterase, feruloyl esterase (EC 3.1.1.73), glucuronoyl esterase (EC 3.1.1.-), α-L-arabinofuranosidase (EC 3.2.1.55), α-arabinopyranosidase (3.2.1.-), α-galactosidase (EC 3.2.1.22), β-galactosidase (EC 3.2.1.23), α-glucuronidase (EC 3.2.1.139), β-mannase (EC 3.2.1.78), β-mannosidase (EC 3.2.1.25), mannan 1,4-mannobiosidase (EC 3.2.1.100), arabinogalactan endo-beta-1,4-galactanase (EC 3.2.1.89), endo-beta-1,3-galactanase (EC 3.2.1.90), galactan endo-beta-1,3-galactanase (EC 3.2.1.181, glucuronoarabinoxylan endo-1,4-beta-xylanase (EC 3.2.1.136), alpha-L-fucosidase (EC 3.2.1.51), coniferin beta-glucosidase (EC 3.2.1.126), xyloglucan hydrolases (EC 3.2.1.150, 151, 155), xylan α-1,2-glucuronosidase (EC 3.2.1.131), endo-xylogalacturonan hydrolases (EC 3.2.1.-; GH28), α-amylase (EC 3.2.1.1), glucan 1,4-α-glucosidase (EC 3.2.1.3), galactan 1,3-galactosidase (GH43), -1,4,-endogalactanases (EC 3.5.1.89; GH53), α-rhamnosidase (EC 3.2.1.40), β-rhamnosidase (EC 3.2.1.43), lignin peroxidase (EC 1.11.1.14), Mn peroxidase (EC 1.11.1.13), aryl-alcohol oxidase (EC 1.1.3.7), glyoxal oxidase (EC 1.1.3.), carbohydrate oxidases (EC 1.1.3.4, 9, 10) and cellobiose dehydrogenase (EC 1.1.99.18).

Within a preferred enzyme-composition the term "hemicellulase" comprises at least one hemicellulase selected from the group of xylanases, xylosidases, esterases, arabinofuranosidases, galactanases, peroxidases and oxidases. It is particularly preferred that the enzyme-composition according to the present invention comprises at least one xylanase, arabinofuranosidase and/or galactanase.

As used within the present invention, the term "pectinase" refers to any enzyme or blend of enzymes capable of degrading or supporting the degradation of pectin.

The at least one pectinase within the enzyme composition according to the present invention is preferably selected from polygalacturonases (EC 3.2.1.15, 67, 82; GH28), pectin-/pectatelyases (EC 4.2.2.2, 6, 9, 10), pectin methyl esterase (EC 3.1.1.11), pectin acetyl esterases (EC 3.1.1.-), rhamnogalacturonases (EC 3.2.1.-; GH28), rhamnogalacturonanacetylesterase (EC 3.1.1.86), rhamnogalacturonanendolyase (EC 4.2.2.23), rhamnogalacturonanlyases (EC 4.2.2.-), rhamnogalacturonangalacturonohydrolases (EC 3.2.1.-), xylogalacturonan hydrolases (EC 3.2.1.-), pectin methylesterase (EC 3.1.1.11), beta-arabinofuranosidase (EC 3.2.1.55), beta-1,4-galactanase (EC 3.2.1.89), beta-1,3-galactanase (EC 3.2.1.90), beta-galactosidase (EC 3.2.1.23), alpha-galactosidase (EC 3.2.1.22), feruloyl acetyl esterases (EC 3.1.1.-), alpha-fucosidase (EC 3.2.1.51), beta-fucosidase (EC 3.2.1.38), beta-apiosidases (EC 3.2.1.-), alpha-rhamnosidase (EC 3.2.1.40), beta-rhamnosidase (EC 3.2.1.43), alpha-arabinopyranosidases (EC 3.2.1.-), beta-glucuronidase (EC 3.2.1.31), alpha-glucuronidase (EC 3.2.1.139), beta-xylosidase (EC 3.2.1.37) and alpha-xylosidases (EC 3.2.1.-).

Within a preferred enzyme-composition the term "pectinase" comprises at least one pectinase selected from the group of pectinesterases, polygalacturonases, pectinlyases, mannosidases and rhamnogalacturonases.

Within a further preferred embodiment of the present invention, the arabinan degrading activity of the Arabinan endo-1,5-alpha-L-arabinosidase (EC 3.2.1.99) is at least 8 times as much as the cellulose degrading activity of the at least one cellulase, preferably at least 18 times as much and most preferred at least 36 times as much as the cellulose degrading activity of the at least one cellulase. Within a further preferred embodiment the arabinan degrading activity of the Arabinan endo-1,5-alpha-L-arabinosidase (EC 3.2.1.99) is 8 to 100 times, preferably 10 to 70 times as much as the cellulose degrading activity of the at least one cellulase.

Within a further preferred embodiment of the present invention, the arabinan degrading activity of the Arabinan endo-1,5-alpha-L-arabinosidase (EC 3.2.1.99) is at least 10 times as much as the pectin degrading activity of the at least one pectinase, preferably at least 25 times as much, also preferred at least 50 times as much and most preferred at least 100 times as much as the pectin degrading activity of the at least one pectinase. Within a further preferred embodiment, the arabinan degrading activity of the Arabinan endo-1,5-alpha-L-arabinosidase (EC 3.2.1.99) is 10 to 250 times, preferably 12 to 100 times, further preferred 15 to 70 times as much as the pectin degrading activity of the at least one pectinase.

Within a further preferred embodiment of the present invention when another hemicellulase is present within the composition, the arabinan degrading activity of the Arabinan endo-1,5-alpha-L-arabinosidase (EC 3.2.1.99) is at least 0.25 times as much as the hemicellulose degrading activity of the at least one hemicellulase, preferably at least 0.5 times as much and most preferred as much as the hemicellulose degrading activity of the at least one hemicellulase. Within a further preferred embodiment the arabinan degrading activity of the Arabinan endo-1,5-alpha-L-arabinosidase (EC 3.2.1.99) is 0.25 to 5 times, preferably 0.5 to 2 times as much as the hemicellulose degrading activity of the at least one hemicellulase.

The enzyme composition according to the present invention preferably lacks any invertase (E.C. 3.2.1.26) enzyme. This is particularly preferred in case the use of the enzyme composition within a process for hydrolyzing biomass is intended to produce granulated sugar for food applications.

The enzymes referenced within the present invention are classified according nomenclatures that are either based on the International Union of Biochemistry and Molecular Biology's Enzyme Nomenclature and Classification (www.chem.qmul.ac.uk/iubmb/enzyme/) or on Carbohydrate-Active EnZYmes (www.cazy.org/) database.

The term "activity" of an enzyme as used within the present invention refers to the catalytic activity of the enzyme under appropriate conditions under which the enzyme serves as a protein catalyst, which converts specific polymeric or artificial substrates to specific oligomeric or monomeric products. In this context the term "appropriate conditions" is well known to and applicable by a person skilled in the art.

In a further aspect, the present invention relates to the use of an enzyme-composition as defined before for hydrolyzing biomass.

The term "biomass" as used within the present invention refers to any type of biomass known to a person skilled in the art as suitable for the inventive process. Particularly preferred is biomass of plant-origin. Within a further preferred embodiment, the initial dry matter content of the biomass is selected from 5 to 50 wt.-%, preferably from 10 to 45 wt.-%, more preferred from 15 to 42 wt.-% and most preferred from 20 to 40 wt.-%. The term "dry matter" (d.m.) refers to the mass to biomass ratio determined after water and other volatile compounds have been removed from fresh tissue using an IR-balance. It is thereby particularly preferred to select a biomass whereby its dry matter contains at least 25 wt.-% of saccharides such as monomeric sugars, dimeric sugars and oligosaccharides and/or polysaccharides, more preferred at least 40 wt.-%, particularly preferred at least 60 wt.-%, further preferred at least 80 wt.-% of saccharides such as monomeric sugars, dimeric sugars and oligosaccharides and/or polysaccharides. Further, any mixtures of suitable biomasses are to be included within the term "biomass".

Particularly preferred biomass is "sugar beet biomass" or "sugar cane biomass". The term "sugar beet biomass" refers to the complete and unprocessed root tissue of Beta vulgaris including the outer peel and the internal pulp. Dry tissue of Beta vulgaris contains 80 wt.-% soluble sucrose, while beet pulp contains approximately 7 wt.-% pectin, 7 wt.-% cellulose and 7 wt.-% hemicellulose, 17 wt.-% arabinose, 20 wt.-% glucose and 3.5 wt.-% fructose and 10 wt.-% proteins, all relative to the dry matter (d.m.) of the biomass. The term "sugar beet biomass" further comprises sugar beet pulp (sugar beet chips).

The term "sugar cane biomass" refers to the complete and unprocessed stalks of Saccharum sp. including the outer peel and the internal pulp. Dry tissue of Saccharum sp. contains 80% wt.-% soluble sucrose, while dry cane bagasse is made up of approximately 70 wt.-% polymeric sugars, including 45 wt.-% cellulose, 23 wt.-% lignin and 25 wt.-% hemicellulose primarily in the form of xylan all relative to the dry matter (d.m.) of the biomass. The term "sugar cane biomass" further comprises sugar cane pressed cake (bagasse).

Further biomass suitable for the process of the present invention comprises waste products from forestry and agriculture, the food-processing and paper industry and communal waste. In particular, the term "biomass" as used within the present invention includes grain straw and spelt (such as wheat, rye, barley, oats), maize straw and spindles, manure from stables, herbaceous materials and grasses such as Sericea lespedeza, switchgrass (Panicumvirgatum), Napier grass (Miscanthus; China reed) and Sudan grass (Sorghum sudananse, Sorghum drummondi), barks, wood chips and chippings, fruit pulp, agave residues, coffee grinds and waste from oil mills such as rapeseed pressed cake and sewage from mills, paper-making stock and waste water from paper mills, waste paper, vegetable and fruit leftovers.

Within a preferred embodiment of the process of the present invention, the biomass is selected from cellulose, hemicellulose and/or lignin-containing biomass.

Within a particularly preferred embodiment of the process of the present invention the biomass is selected from sugar beet, sugar cane, straw, corn, wood, oilseed and mixtures thereof.

In a further aspect, the present invention relates to a process for hydrolyzing biomass comprising the steps
a) Contacting the biomass with an enzyme-composition as defined above;
b) Subjecting at least one part of the biomass to a filtration and separating the permeate.

According to the present invention, the "contacting" may be carried out by any method known to a person skilled in the art as suitable for the inventive process. Within a preferred embodiment, the "contacting" of the biomass with the enzyme-composition is carried out by adding the enzyme-composition to the biomass. Preferably, the contacting is followed by mixing the biomass with the enzyme-composition.

During the contacting of the biomass with the enzyme-composition the temperature is preferably selected from 25 to 80° C., more preferred selected from 45 to 75° C. and particularly preferred from 48 to 70° C.

Within a particularly preferred embodiment, the process for hydrolyzing biomass is carried out for 1 minute to 100 hours, more preferred for 10 minutes to 80 hours, particularly preferred for 30 minutes to 40 hours, even more preferred for 1 hour to 30 hours also particularly preferred from 2 hours to 20 hours and most preferred from 3 to 12 hours.

In another preferred embodiment, step (a) of the process for hydrolyzing biomass is carried out for 1 to 80 hours, preferably 2 to 40 hours, more preferred 3 to 20 hours wherein the temperature is selected from 45 to 75° C. or from 48 to 70° C.

It is thereby possible to select different temperatures for certain time periods while carrying out step a) of the process of the present invention. Within another preferred embodiment of the process for hydrolyzing biomass, step a) of the process is preferably carried out for a first time period of from 1 to 5 hours, preferably 2 to 3 hours at a temperature from 35 to 45° C., preferably 40° C.; subsequently for a second time period of from 1 to 5 hours, preferably 2 to 3 hours at a temperature from more than 45 to 55° C., preferably 50° C.; subsequently for a third time period of from 1 to 4 hours, preferably 1.5 to 2 hours at a temperature from more than 55 to 65° C., preferably 60° C. It is a particular advantage of the enzyme-composition of the present invention that following a subsequent increase of the process-temperature over time as outlined before, a further increase of the efficiency and hydrolysis of the biomass may be achieved. The enzyme composition is preferably added to the biomass in an amount of from 0.025 to 8 wt.-% of the initial dry matter of the biomass, more preferred 0.05 to 4 wt.-% of the dry matter of the biomass, particularly preferred being 0.08 to 2 wt.-% of the dry matter of the biomass and most preferred from 0.1 to 0.2 wt.-% of the dry matter of the biomass.

Within a further preferred embodiment, the initial dry matter content of the biomass is selected from 5 to 50 wt.-%, preferably from 10 to 45 wt.-%, more preferred from 15 to 42 wt.-% and most preferred from 20 to 40 wt.-%. The term "dry matter" (d.m.) refers to the mass to biomass ratio determined after water and other volatile compounds have been removed from fresh tissue using an IR-balance.

Within a further preferred embodiment, the biomass is contacted with all enzyme blends and the Arabinan endo-1, 5-alpha-L-arabinosidase (EC 3.2.1.99) of the inventive enzyme composition at the same time, it is however also possible to contact the biomass stepwise with the different enzyme blends and the Arabinan endo-1,5-alpha-L-arabinosidase (EC 3.2.1.99) of the inventive enzyme composition.

Within a further preferred embodiment, the process for hydrolyzing biomass is carried out until the content of remaining dry insoluble solids within the biomass is less than 30 wt.-%, preferably less than 10 wt.-%, even more preferred less than 2.5 wt.-%. In a further preferred embodiment, step (a) of the process for hydrolyzing biomass is carried out until the content of remaining dry insoluble solids within the biomass is from 0.5 to 30 wt.-%, preferably from 1 to 10 wt.-% and most preferred from 1.5 to 5 wt.-%.

The term "dry insoluble solids" refers to the mass of insoluble solids determined after water and other volatile compounds have been removed from the solid fraction using an IR-balance to the mass of the total sample including both the liquid fraction and the solid fraction. The solid fraction of the sample can be separated from the liquid fraction by e.g. centrifugation.

The pH of the biomass is preferably selected from 3 to 9, preferably from 4 to 6, even more preferred from 4.5 to 5.5.

Within a preferred embodiment of the process for hydrolyzing biomass the filtration is either an ultrafiltration or a microfiltration. Within a particularly preferred embodiment, the ultrafiltration is carried out by use of an ultrafiltration membrane which is further preferred a ceramic membrane, a stainless steel membrane, a synthetic membrane (preferably comprising polysulfone) or silicon or silicon-containing membrane or any combination thereof. Within a further particularly preferred embodiment, the cut-off of the membrane is selected from 0.5 kDa to 100 kDa, more preferred from 1 kDa to 50 kDa, even more preferred from 2 kDa to 25 kDa. Within a further particularly preferred embodiment, the microfiltration is carried out by use of an microfiltration membrane which is further preferred a ceramic membrane, a stainless steel membrane, a synthetic membrane (preferably comprising polysulfone) or silicon or silicon-containing membrane or any combination thereof.

Particularly Preferred Embodiments of the Present Invention

The following embodiments are to be understood as particularly preferred embodiments only and not limiting the scope of the present invention in any respect.

A) Enzyme-composition comprising at least one cellulase selected from cellobiohydrolases (EC 3.2.1.-), endo-1,4-β-glucanase (EC 3.2.1.4), β-glucosidase (EC 3.2.1.4) cellobiose hydrolase (EC 3.2.1.21), glycoside hydrolase 61 (GH61 and CBM33), Expansin, Swollenin, Loosinin and CIP Proteins (EC 3.1.1.-; CE15), at least one hemicellulase selected from xylanases, xylosidases, esterases, arabinofuranosidases, galactanases, peroxidases and oxidases and at least one pectinase selected from pectinesterases, polygalacturonases, pectinlyases, mannosidases and rhamnogalacturonases, wherein the at least one hemicellulase comprises an Arabinan endo-1,5-alpha-L-arabinosidase (EC 3.2.1.99) with an arabinan degrading activity of at least 10 U/mg protein.

Within this particular preferred embodiment it is further preferred that the arabinan degrading activity of the Arabinan endo-1,5-alpha-L-arabinosidase (EC 3.2.1.99) is at least 8 times, preferably 8 to 100 times, as much as the cellulose degrading activity of the at least one cellulase and/or at least 10 times, preferably 10 to 250 times, as much as the protein degrading activity of the at least one pectinase and/or at least 0.25 times, preferably 0.25 to 5 times, as much as the hemicellulose degrading activity of the at least one hemicellulase.

B) Enzyme-composition comprising at least one cellulase selected from cellobiohydrolases (EC 3.2.1.-) and endo-1,4-β-glucanase (EC 3.2.1.4), at least one hemicellulase selected from xylanases, arabinofuranosidases and galactanases and at least one pectinase selected from polygalacturonases, pectinlyases and rhamnogalacturonases, wherein the at least one hemicellulase comprises an Arabinan endo-1,5-alpha-L-arabinosidase (EC 3.2.1.99) with an arabinan degrading activity of at least 10 U/mg protein.

Within this particular preferred embodiment it is further preferred that the arabinan degrading activity of the Arabinan endo-1,5-alpha-L-arabinosidase (EC 3.2.1.99) is at least 8 times, preferably 8 to 100 times, as much as the cellulose degrading activity of the at least one cellulase and/or at least 10 times, preferably 10 to 250 times, as much as the protein degrading activity of the at least one protease and/or at least 0.25 times, preferably 0.25 to 5 times, as much as the hemicellulose degrading activity of the at least one hemicellulase.

C) Process for Hydrolyzing Biomass Comprising the Steps
  a) Contacting the biomass with an enzyme-composition as defined above within embodiment A or B;
  b) Subjecting at least one part of the biomass to a filtration and separating the permeate,
  wherein step a) of the process is carried out for a first time period of from 1 to 5 hours, preferably 2 to 3 hours at a temperature from 35 to 45° C., preferably 40° C.; subsequently for a second time period of from 1 to 5 hours, preferably 2 to 3 hours at a temperature from more than 45 to 55° C., preferably 50° C.; subsequently for a third time period of from 1 to 4 hours, preferably 1.5 to 2 hours at a temperature from more than 55 to 65° C., preferably 60° C.

and/or wherein the biomass is selected from sugar-beet, sugar-cane, straw, corn, wood, oilseed and compositions thereof and/or wherein the dry matter content of the biomass is selected from 5 to 50 wt.-%, preferably from 10 to 45 wt.-%, more preferred from 15 to 42 wt.-% and most preferred from 20 to 40 wt.-%.

Methods

The following methods were used within the examples of the present invention:

Enzyme Assays

Arabinase-Assay

The activity of arabinase is determined using Red Debranched Arabinan as substrate (S-RDAR®, Megazyme International, Ireland). The reaction mixtures (200 µL) contain 100 µL of enzyme solution and 20 mg/mL Red Debranched Arabinan (final concentration) in 50 mM sodium acetate buffer (pH5) are incubated for 0, 5, 10, 15, 20, 25 and 30 min at 50° C. The amount of red dye released is measured at A520 after addition of EtOH 95% to the reaction mixtures and further incubation for 10 minutes. One unit (U) of Red Debranched Arabinan hydrolyzing activity is defined as the amount of enzyme equivalent to release 1AU (absorption unit) of red dye per minute under above described conditions (pH5, 50° C. and 20 mg/mL substrate concentration).

Protein-Assay

Protein concentrations were determined according to the Bradford method (Bradford M. M. (1976). Anal. Biochem. 72, 248-254).

Enzyme Compositions

The following enzymes were used for preparing enzyme-compositions:

Arabinase (E-EARAB, Megazymes® Inc., Ireland), cellulase (Celluclast®, Novozymes®, Denmark), beta-glucosidase (Novo 188®, Novozymes®, Denmark), and pectinase (Pectinex Ultra SP-L®, Novozymes, Denmark). Where necessary, enzymes were desalted and concentrated with 45 ml sodium acetate buffer (50 mM, pH 5) using 50 ml Amicon ultrafiltration devices (10 kDa cut-off; Millipore®, Maidstone, UK).

Reference Enzyme Composition

The following enzymes were used: 43.4 wt.-% Celluclast®, 6.3 wt.-% Novo 188® and 50.3 wt.-% Pectinex Ultra SP-L®. These products were mixed in 50 mMNaAc buffer (pH 5).

Enzyme Composition According to the Present Invention (EC)

The following enzymes were used: 43.4 wt.-% Celluclast®, 6.3 wt.-% Novo 188® and 50.3 wt.-% Pectinex Ultra SP-L® with 5 wt.-% arabinan endo-1,5-alpha-L-arabinosidase (E-EARAB, Megazymes® Inc., Ireland). These products were mixed in 50 mMNaAc buffer (pH 5).

EXAMPLES AND FIGURES

The present invention is now described by the following examples and figures. All examples and figures are for illustrative purposes only and are not to be understood as limiting the invention.

FIG. 4 shows the improved arabinose release from sugar beet roots after 24 hours at 50° C. depending on the arabinan endo-1,5-alpha-L-arabinase added to the reference enzyme composition.

EXAMPLE 1: ENZYMATIC LIQUEFACTION OF WHOLE SUGAR BEET AT 50° C.

Whole sugar beet material was prepared from fresh sugar beet roots sampled in Sulzemoos, Germany. Beet roots were washed to remove remaining soil and cut into approx. 10 mm×10 mm pieces using a Waring blender. The sugar beet material had an average d.m. content of 23%.

The reaction mixture (20 mL) contained 0.1% E/S of the enzyme-composition according to the present invention (EC) or of the reference enzyme-composition and a d.m. content of 15% sugar beet in 50 mM sodium acetate buffer (pH5). The reaction mixture was incubated for 30 min to 5 hours at 50° C. After liquefaction and hydrolysis the reaction mixture was centrifuged for 30 min at 3200 g and the liquid supernatant was separated and weighted. 1 ml of the supernatant was heat inactivated at 95° C. for 10 min and the amount of sugar released was analyzed by HPLC (Agilent®, Germany) with an Aminex® HPX 87 (BioRad Labs, Hercules, USA) ion exchange column (Eluent: 100% water, T: 85° C., Flow: 0.6 ml/min, RI detection).

The liquefaction was determined according the formula:

$$\frac{\text{net weight of supernatant}}{20} \times 100.$$

Figure 1:
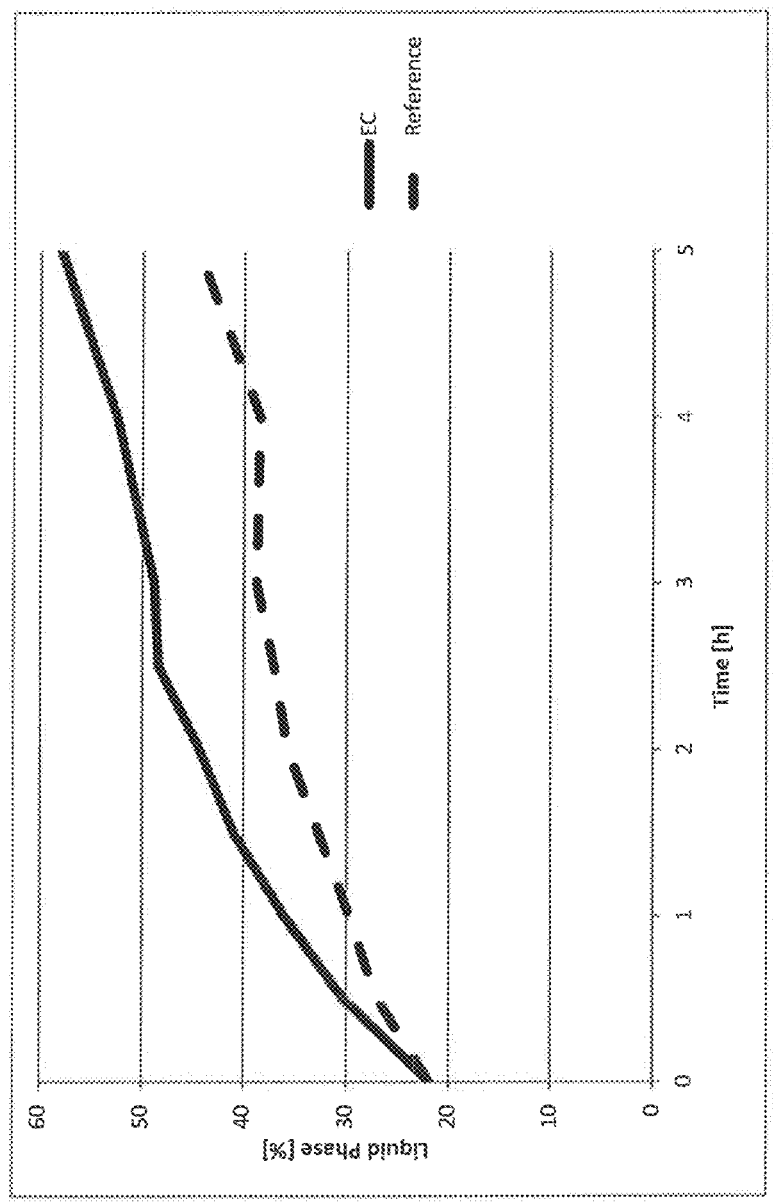
FIG. 1 shows the improved liquefaction of sugar beet roots within the first 5 hours for the enzyme-composition according to the present invention (EC) compared to the reference enzyme-composition at 50° C.
Figure 2:
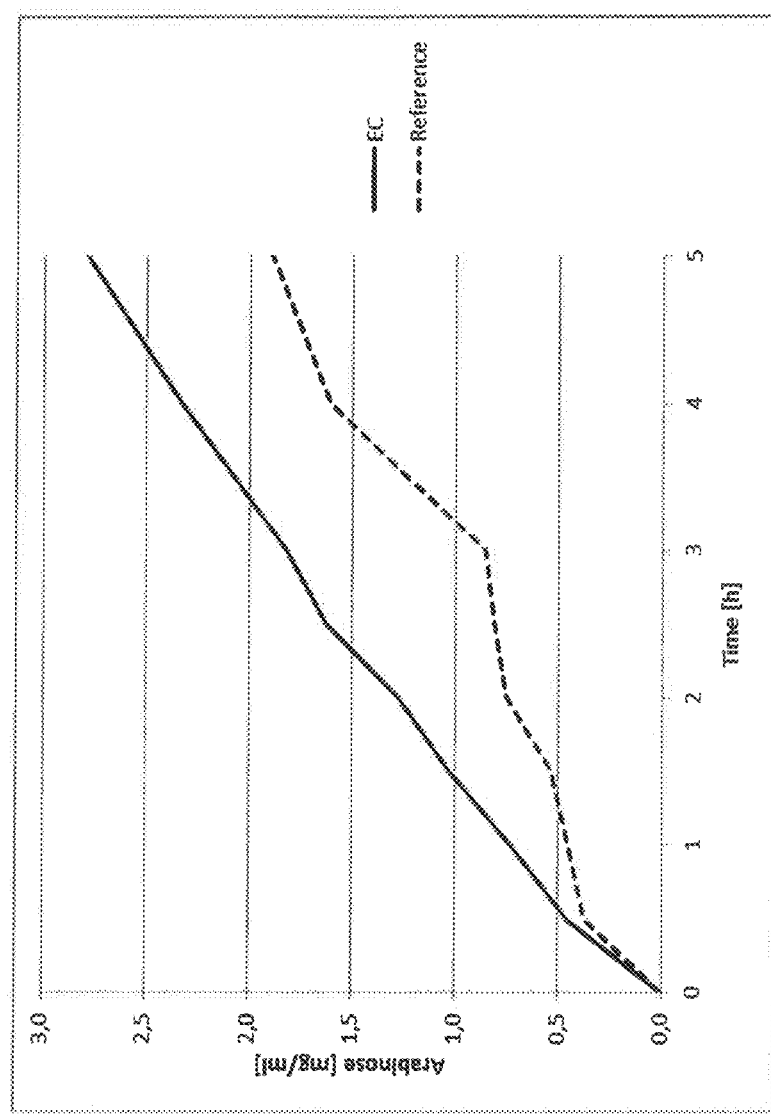
FIG. 2 shows the improved arabinose release from sugar beet roots within the first 5 hours for the enzyme-composition according to the present invention (EC) compared to the reference enzyme-composition at 50° C.

The results are shown in FIGS. 1 and 2.

EXAMPLE 2: ENZYMATIC LIQUEFACTION OF WHOLE SUGAR BEET AT DIFFERENT ACTIVITIES OF ARABINAN ENDO-1,5-ALPHA-L-ARABINANASE

The reaction mixture (20 mL) contained 0.05% E/S of Reference enzyme blend and variable amounts arabinan endo-1,5-alpha-L-arabinanase. The d.m. content was set to 15% by addition of 50 mM sodium acetate buffer (pH5). The reaction mixture was incubated for 24 h at 50° C. After liquefaction and hydrolysis the reaction mixture was centrifuged for 30 min at 3200 g and the liquid supernatant was separated and weighted. 1 ml of the supernatant was heat inactivated at 95° C. for 10 min and the amount of sugar released was analyzed by HPLC (Agilent®, Germany) with an Aminex® HPX 87 (BioRad Labs, Hercules, USA) ion exchange column (Eluent: 100% water, T: 85° C., Flow: 0.6 ml/min, RI detection).

The liquefaction was determined according the formula:

$$\frac{\text{net weight of supernatant}}{20} \times 100.$$

Figure 3:
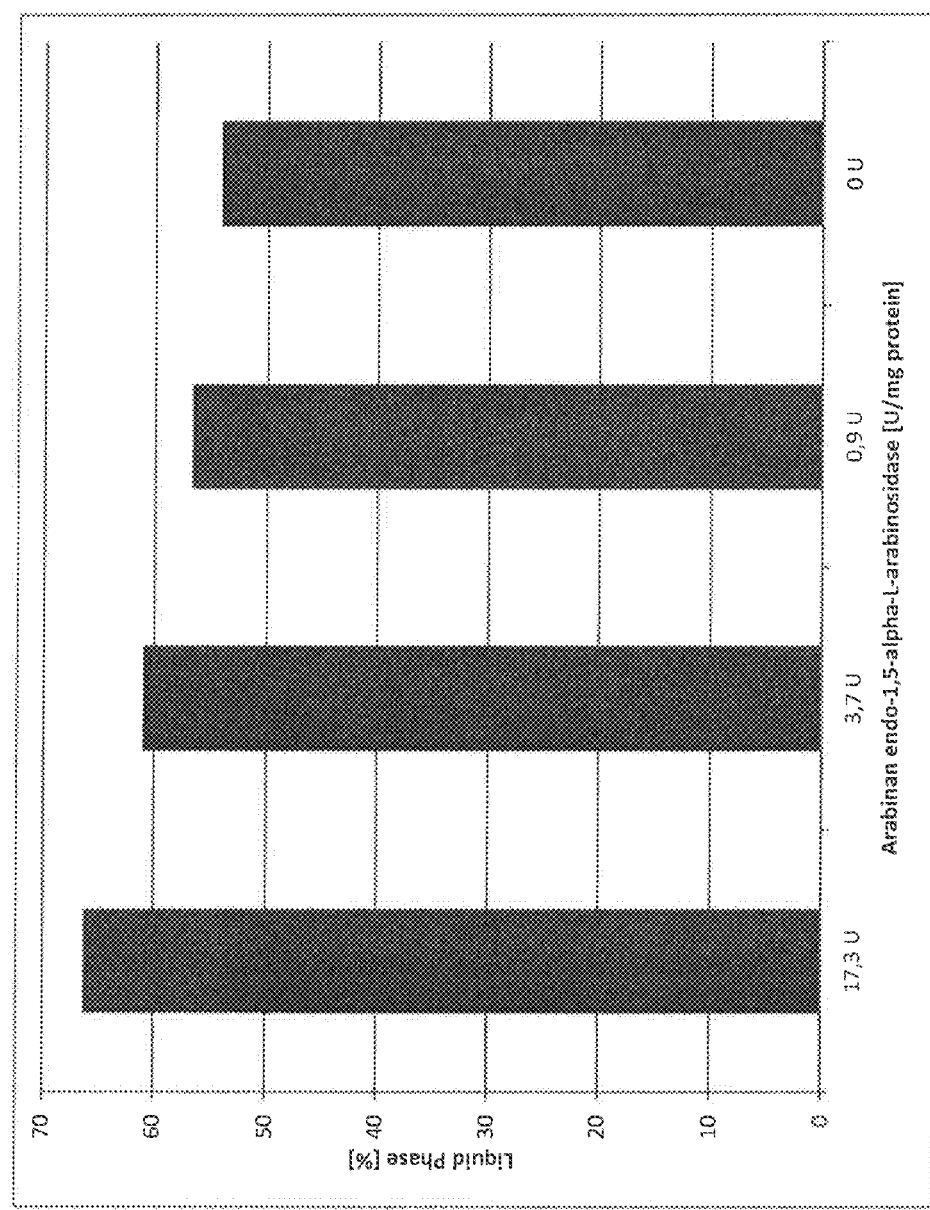
FIG. 3 shows the improved liquefaction of sugar beet roots after 24 hours at 50° C. depending on the arabinan endo-1,5-alpha-L-arabinase added to the reference enzyme composition.

The results are shown in FIGS. 3 and 4.

What is claimed is:

1. An enzyme composition comprising:
   at least one cellulase,
   at least one hemicellulase and
   at least one pectinase,
   wherein said at least one cellulase comprises at least one enzyme selected from the group consisting of cellobiohydrolases and endo-1,4-β-glucanase;
   wherein said at least one hemicellulase comprises an Arabinan endo-1,5-alpha-L-arabinosidase (EC 3.2.1.99) and the arabinan degrading activity of the Arabinan endo-1,5-alpha-L-arabinosidase (EC 3.2.1.99) is at least 8 times as much as the cellulose degrading activity of the at least one cellulase;
   wherein said at least one pectinase comprises at least one enzyme selected from the group consisting of pectinesterases, polygalacturonases, pectinlyases, mannosidases and rhamnogalacturonases;
   wherein the arabinan degrading activity of the Arabinan endo-1,5-alpha-L-arabinosidase (EC 3.2.1.99) is at least 10 times as much as the pectin degrading activity of the at least one pectinase;
   wherein said at least one cellulase, said one least one hemicellulase, and said at least one pectinase are in a non-naturally occurring ratio; and
   wherein said enzyme-composition provides improved arabinose yield and liquefaction.

2. The enzyme composition enzyme composition of claim 1,
   wherein said enzyme-composition further comprises at least one hemicellulase selected from the group consisting of xylanases, xylosidases, esterases, arabinofuranosidases, galactanases, peroxidases and oxidases.

3. The enzyme-composition of claim 1, wherein the arabinan degrading activity of the Arabinan endo-1,5-alpha-L-arabinosidase (EC 3.2.1.99) is at least 10 times as much as the pectin degrading activity of the at least one pectinase.

4. The enzyme composition of claim 2, wherein the arabinan degrading activity of the Arabinan endo-1,5-alpha-L-arabinosidase (EC 3.2.1.99) is at least 0.25 times as much as the hemicellulose degrading activity of the at least one xylanase, xylosidase, esterase, arabinofuranosidase, galactanase, peroxidase and/or oxidase.

5. The enzyme composition of claim 1, wherein the hemicellulases, cellulases and/or pectinases are produced by expression in *Trichoderma reesei*.

* * * * *